United States Patent [19]

Chekroun et al.

[11] Patent Number: 5,312,920
[45] Date of Patent: May 17, 1994

[54] PROCESS FOR PREPARING 4-PYRIMIDINONES

[75] Inventors: Isaac Chekroun, Epinay; Manuel Bedoya Zurita, Paris; José Ruiz-Montes, Mantes la Jolie; Guy Rossey, Voisins le Bretonneux, all of France

[73] Assignee: Synthelabo, Le Plessis Robinson, France

[21] Appl. No.: 30,545

[22] Filed: Mar. 12, 1993

[30] Foreign Application Priority Data

Mar. 16, 1992 [FR] France ................. 92 03115

[51] Int. Cl.$^5$ .................................. C07D 403/10
[52] U.S. Cl. ........................................... 544/319
[58] Field of Search ............................. 544/319

[56] References Cited

U.S. PATENT DOCUMENTS 5,130,439 7/1992 Lo et al. ..................... 548/110
5,166,206 11/1992 Allen ......................... 544/319

FOREIGN PATENT DOCUMENTS 407342 1/1991 European Pat. Off. .

Primary Examiner—John M. Ford
Attorney, Agent, or Firm—Jacobson, Price, Holman & Stern

[57] ABSTRACT

A process for preparing a compound represented by formula

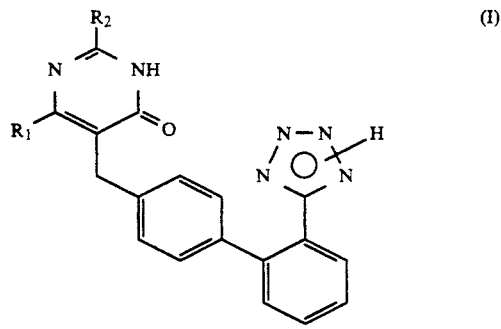

(I)

by deprotecting a compound represented by formula (VII)

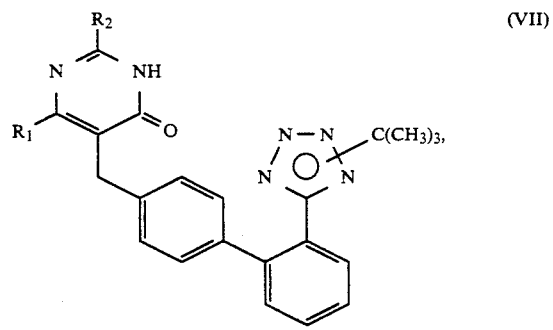

(VII)

in which $R_1$ represents an unbranched or branched $C_{1-7}$ alkyl, unbranched or branched $C_{3-9}$ alkenyl, or $(C_{3-7})$cycloalkyl$(C_{1-6})$alkyl, and $R_2$ represents hydrogen, unbranched or branched $C_{1-7}$ alkyl, $(C_{3-7})$cycloalkyl$(C_{1-3})$alkyl, aryl$(C_{1-3})$alkyl optionally substituted on the ring-system, aryloxy$(C_{1-3})$alkyl optionally substituted on the ring-system, arylthio$(C_{1-3})$alkyl optionally substituted on the ring-system, arylsulphonyl$(C_{1-3})$alkyl optionally substituted on the ring-system, and heteroaryl$(C_{1-3})$alkyl optionally substituted on the ring-system.

13 Claims, No Drawings

PROCESS FOR PREPARING 4-PYRIMIDINONES

FIELD OF THE INVENTION

The present invention relates to novel 4-pyrimidinones, to a process for their preparation and to their use in preparing other 4-pyrimidinones. The invention also relates to intermediates used in the process.

SUMMARY OF THE INVENTION

According to the invention there is provided a compound represented by formula (VII)

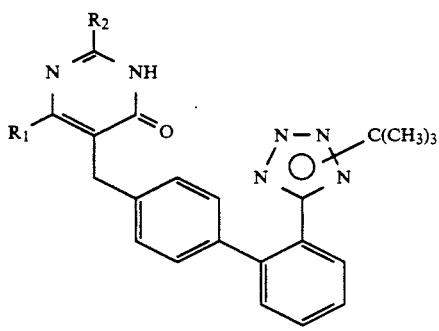
(VII)

in which
$R_1$ represents a substituent selected from unbranched or branched $C_{1-7}$ alkyl, unbranched or branched $C_{3-9}$ alkenyl and $(C_{3-7})$cycloalkyl $(C_{1-6})$ alkyl, $R_2$ represents a substituent selected from hydrogen, unbranched or branched $C_{1-7}$ alkyl, $(C_{3-7})$cycloalkyl$(C_{1-3})$alkyl, aryl$(C_{1-3})$alkyl optionally substituted on the ring-system, aryloxy$(C_{1-3})$alkyl optionally substituted on the ring system, arylthio$(C_{1-3})$alkyl optionally substituted on the ring-system, arylsulphonyl$(C_{1-3})$alkyl optionally substituted on the ring-system, and heteroaryl$(C_{1-3})$alkyl optionally substituted on the ring-system.

A compound represented by formula (VII) is useful in a process for preparing a compound represented by formula (I)

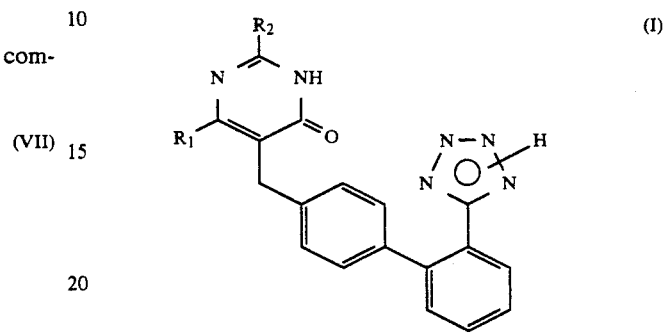
(I)

in which $R_1$ and $R_2$ are as defined above, which process comprises deprotecting a compound represented by formula (VII) as defined above. The invention also provides a process for preparing a compound represented by formula (VII).

DETAILED DESCRIPTION OF THE INVENTION

A process according to the invention is described in Scheme 1:

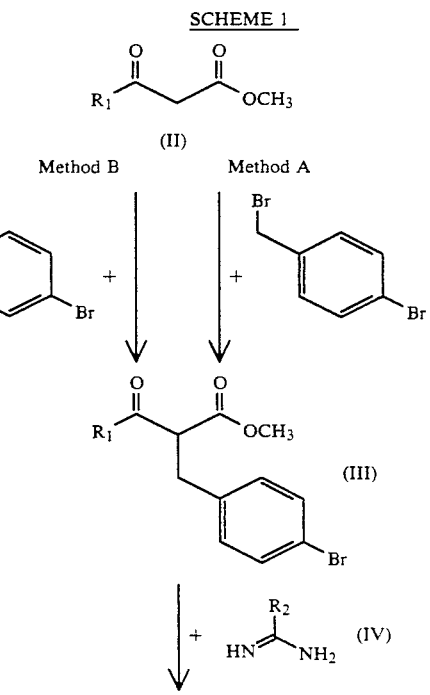

SCHEME 1

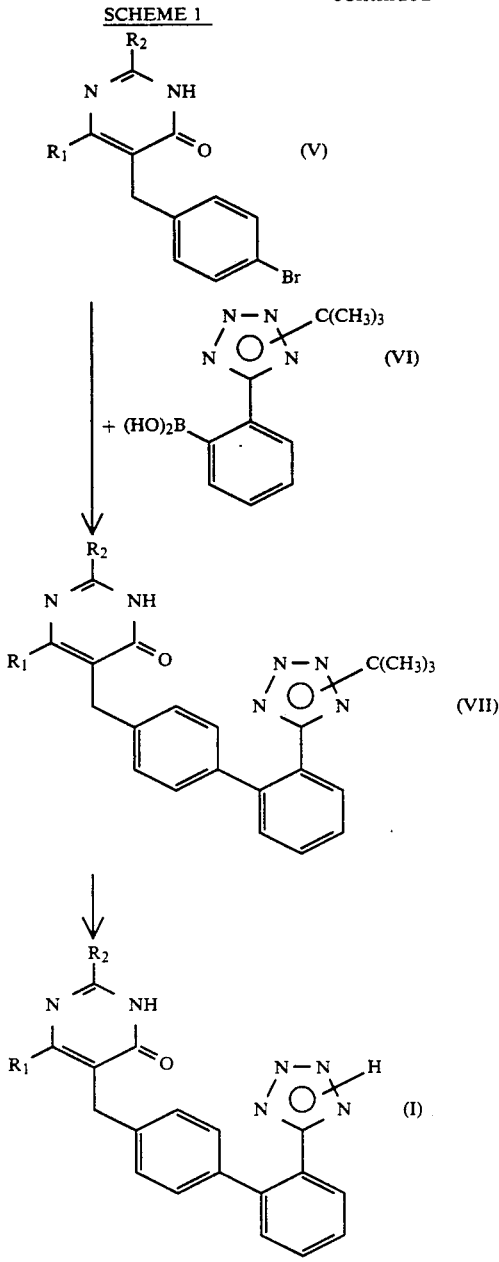

In a first step,
either a β-keto ester of general formula (II), in which R₁ is defined as above, is reacted with 1-bromo-4-(bromomethyl)benzene (Method A) to obtain a compound of general formula (III). The reaction is carried out in a solvent such as methanol, ethanol, 1,1-dimethylethanol, dimethylformamide, dimethyl sulphoxide, acetonitrile or 1-methylpyrrolidinone, in the presence of a base such as sodium hydride, lithium hydride, potassium 1,1-dimethylethylate or an alkali metal carbonate, and optionally in the presence of a catalyst such as lithium bromide or iodide, magnesium bromide or iodide or zinc bromide or iodide.
or a β-keto ester of general formula (II), in which R₁ is defined as above, is reacted with 4-bromobenzaldehyde (Method B) to obtain a bromo derivative, which is reduced to a compound of general formula (III). The first reaction is carried out in a solvent such as toluene, in the presence of a base such as piperidine; the reduction is carried out in the presence of magnesium, in a solvent such as methanol.

In a second step, a β-keto ester of general formula (III) is reacted with an amidine of general formula (IV), in which R₂ is defined as above, to obtain a 5-[(4-bromophenyl)methyl]-4-pyrimidinone of general formula (V), in which R₁ and R₂ are as defined before. The reaction is performed in a solvent such as toluene.

In a third step, a pyrimidinone of general formula (V) is reacted with a boronic acid derivative of formula (VI) to obtain a compound of general formula (VII). The reaction is performed in a solvent such as toluene, in the presence of a base such as sodium carbonate and a catalyst such as tetrakis(triphenylphosphine)palladium.

The compounds of formula (VI) are prepared from 5-phenyltetrazole of formula (A), according to the following scheme:

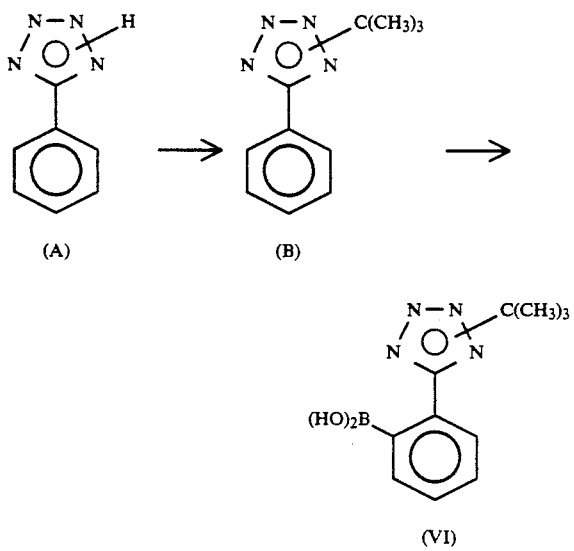

The tetrazolyl group of 5-phenyltetrazole (A) is protected with a 1,1-dimethylethyl group according to the method described for an analogous derivative by J. W. Tilley et al., J.Med. Chem. 1991, 34, 1125-1126, and the compound (B) obtained is reacted with an alkyllithium such as butyllithium in an aprotic solvent such as tetrahydrofuran, at a temperature of between −50° C. and +20° C. An organolithium derivative is obtained and is reacted with trialkyl borate in a solvent such as tetrahydrofuran. An alkyl benzeneboranate is obtained, which is subjected to a hydrolysis reaction.

In a fourth step, deprotection of the tetrazole group of the compounds of general formula (VII) is carried out by heating in a strong acid, such as, for example, aqueous hydrobromic acid, hydrobromic acid dissolved in acetic acid, sulphuric acid or acetic acid, in the presence of boron trifluoride etherate, to obtain the compounds of general formula (I).

The invention includes a compound represented by formula (V)

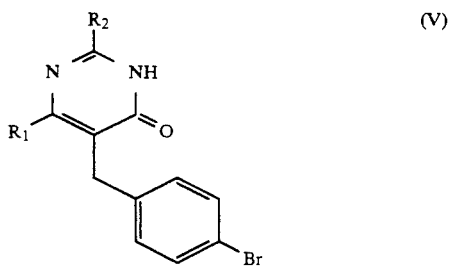

in which $R_1$ and $R_2$ are as defined above.

The Example which follows illustrates the invention. The analyses confirm the structure of the products obtained.

EXAMPLE 1

6-Butyl-2-(2-Phenylethyl)-5-[[2'-(2H-Tetrazol-5-yl)-1,1'-Biphenyl-4-yl]Methyl]-4(3H)-Pyrimidinone.

1.1. Methyl 2-[(4-bromophenyl)methyl]-3-oxoheptanoate

Method A 5.16 g of potassium 1,1-dimethylethylate and 60 ml of dimethylformamide are introduced into a 250-ml three-necked round-bottomed flask maintained under nitrogen. The mixture is cooled to 4°–5° C. There follows the dropwise addition in the course of 45 minutes of a solution of 7.28 g (46 mmol) of methyl oxoheptanoate in 18 ml of dimethylformamide, and then 8.7 g of lithium bromide. After 15 minutes' stirring, a solution of 10 g (40 mmol) of 1-bromo-4-(bromomethyl)benzene in a dimethylformamide/tetrahydrofuran (1:1) mixture is added. The mixture is left overnight at room temperature and filtered and the solution is evaporated under vacuum. The residue is then taken up in dichloromethane, and the organic phase is washed with water, dried over magnesium sulphate and thereafter evaporated to dryness. An orange oil is obtained, which is purified by filtration through silica. The fractions containing the pure product are combined and evaporated to dryness under vacuum.

8.6 g of yellow oil are obtained. The NMR spectrum is compatible with the structure of the product.

Yield=65.6%

Method B a) Methyl 2-[(4-bromophenyl)methylene]-3-oxoheptanoate

A mixture of 1.58 g (10 mmol) of methyl 3-oxoheptanoate, 1.85 g (10 mmol) of 4-bromobenzaldehyde, 0.04 ml of piperidine, 0.12 ml of acetic acid and 10 ml of toluene is heated to the refluxing temperature in a 25-ml round-bottomed flask equipped with a Dean and Stark apparatus. After two hours of heating, the theoretical amount of water is recovered and the toluene is evaporated off under vacuum.

3.1 g of product are obtained in the form of a light yellow oil, a mixture of the two (Z and E) isomers.

Yield=95.3% b) Methyl 2-[(4-bromophenyl)methyl]-3-oxoheptanoate 1.8 g (5.5 mmol) of the benzylidene derivative obtained above in a), 10 ml of anhydrous methanol and 0.5 g of magnesium turnings are introduced into a 25-ml round-bottomed flask. The reaction mixture is brought to the refluxing temperature and allowed to return to room temperature. It is cooled to 0° C. and neutralised by the slow addition of acetic acid to pH 3. The mixture is filtered and evaporated under vacuum. The residue is taken up with ethyl acetate, and the organic phase is washed with water, dried and evaporated to dryness.

1.6 g of yellow oil are obtained. The NMR spectrum is compatible with the structure of the product.

Yield=88.4%

1.2. 5-[(4-Bromophenyl)methyl]-6-butyl-2-(2-phenylethyl)-4(3H)-pyrimidinone 8.4 g (25.67 mmol) of the keto ester obtained above and 17 ml of toluene are introduced into a 50-ml round-bottomed flask. The solution is brought to reflux. 6.5 g (43.86 mmol) of 3-benzenepropanamidine are added in small portions in the course of 4 hours. After 4 hours 30 minutes, the mixture is evaporated to dryness under vacuum and the residue is ground in 30 ml of 1,1-dimethylethyl methyl ether. The solid is filtered off, washed with ice-cold 1,1-dimethylethyl methyl ether and dried under vacuum.

7 g of product are obtained.

Melting point=159°-161.5° C. Yield=64.2%

1.3.
6-Butyl-5-[[2'-[2-(1,1-dimethylethyl)-2H-tetrazol-5-yl]-1,1'-biphenyl-4-yl]methyl]-2-(2-phenylethyl)-4(3H)-pyrimidinone 1.2 g (4.8 mmol) of 2-[2-(1,1-dimethylethyl)-2H-tetrazol-5-yl]benzeneboronic acid, 2.07 g (4.8 mmol) of the bromo derivative obtained above, 0.28 g (0.24 mol) of tetrakis(triphenylphosphine)palladium, 5 ml of 2M sodium carbonate solution and 25 ml of toluene are introduced successively into a two-necked round-bottomed flask equipped with a condenser. This mixture is brought to the refluxing temperature for 16 hours. After cooling and when settling has taken place, the aqueous phase is extracted with 150 ml of ethyl acetate. The organic phases are combined and washed successively with 20 ml of water and then with 20 ml of saturated sodium chloride solution. They are dried over magnesium sulphate. After evaporation of the solvent, the residue is purified by chromatography on a column of silica gel, eluting with an ethyl acetate/hexane (1:4) mixture.

1.42 g of product are obtained in the form of a white solid.

Melting point=143°-145° C. Yield=53.4%

1.4.
6-Butyl-2-(2-phenylethyl)-5-[[2'-(2H-tetrazol-5-yl)-1,1'-biphenyl-4-yl]methyl]-4(3H)-pyrimidinone.

1.1. Methyl 2-[(4-bromophenyl)methyl]-3-oxoheptanoate 1 g of the derivative obtained above in 1.3 in 10 ml of 60% hydrobromic acid is introduced into a 25-ml round-bottomed flask. The mixture is heated for 20 minutes to 120° C. and then poured into ice-cold water. The precipitate obtained is washed with water and dissolved in a minimum volume of methanol. The mixture is alkalinised with aqueous sodium bicarbonate, diluted with water and neutralised with acetic acid. The product is filtered off and washed with water and with methanol. It is dried under vacuum.

0.8 g of the expected compound is obtained.

Melting point=227° C. Yield=89.3%

The process according to the invention enables the compounds (I) to be obtained in good yield.

We claim:

1. A process for preparing a compound represented by formula (I):

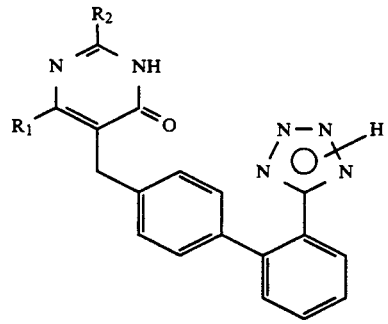

in which $R_1$ is selected from the group consisting of hydrogen, unbranched and branched $C_{1-7}$ alkyl, unbranched and branched $C_{3-9}$ alkenyl, and $(C_{3-7})$cycloalkyl$(C_{1-6})$alkyl groups, and $R_2$ is selected from the group consisting of hydrogen, unbranched and branched $C_{1-7}$ alkyl, $(C_{3-7})$cycloalkyl$(C_{1-3})$alkyl, aryl$(C_{1-3})$alkyl, aryloxy$(C_{1-3})$alkyl, arylthio$(C_{1-3})$alkyl, arylsulphonyl$(C_{1-3})$alkyl and heteroaryl $(C_{1-3})$ alkyl groups, said process comprising the steps of reacting a compound of general formula (II):

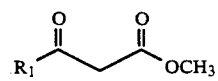

in which $R_1$ is as defined above, with 1-bromo-4-(bromomethyl)benzene or 4-bromobenzaldehyde, and reducing the product compound formed to obtain a compound represented by formula (III):

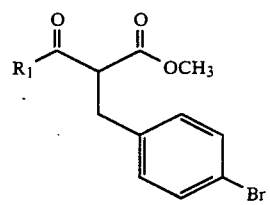

in which $R_1$ is as defined above, reacting the compound represented by formula (III) with an amidine of general formula (IV):

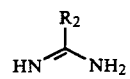

in which $R_2$ is as defined above to obtain a compound represented by formula (V):

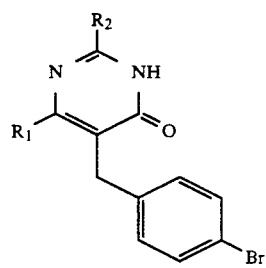

in which $R_1$ and $R_2$ are as defined above, reacting the compound represented by formula (V) with a compound represented by formula (VI):

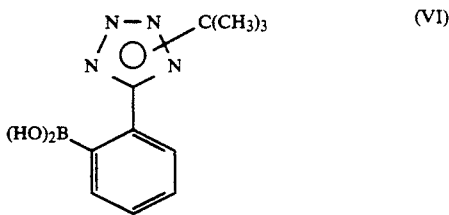

to obtain a compound represented by formula (VII):

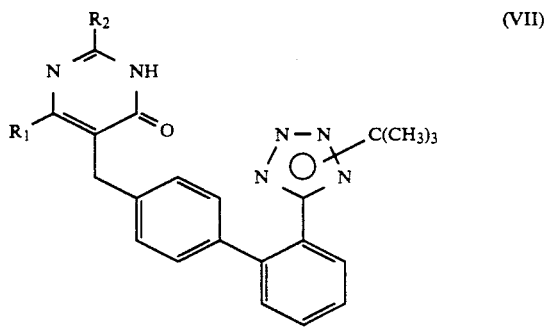

in which $R_1$ and $R_2$ are as defined above, and deprotecting the compound represented by formula (VII) by removing the protecting group $-C(CH_3)_3$ from the tetrazole moiety of the compound of formula (VII).

2. A process according to claim 1, wherein the reaction between the compound represented by formula (V) and the compound represented by formula (VI) is carried out in a solvent, and in the presence of a base and a catalyst.

3. A process according to claim 2, wherein the solvent is toluene, the base is sodium carbonate and the catalyst is tetrakis(triphenylphosphine)palladium.

4. A process according to claim 1, wherein the reaction between the compound represented by formula (III) and the compound represented by formula (IV) is performed in a solvent.

5. A process according to claim 4, wherein the solvent is toluene.

6. A process according to claim 1, wherein the reduction which yields the compound represented by formula (III) is carried out with magnesium and in a solvent.

7. A process according to claim 6, wherein the solvent is methanol.

8. A process according to claim 1, wherein the compound represented by formula (II) is reacted with 4-bromobenzaldehyde in a solvent and in the presence of a base.

9. A process according to claim 8, wherein the solvent is toluene and the base is piperidine.

10. A process according to claim 1, wherein the compound represented by formula (II) is reacted with 1-bromo-4-(bromomethyl)benzene in a solvent, in the presence of a base.

11. A process according to claim 10, wherein the solvent is dimethylformamide, and the base is potassium 1,1-dimethylethylate.

12. A process according to claim 1, wherein the compound represented by formula (II) is reacted with 1-bromo-4-(bromomethyl)benzene in a solvent, in the presence of a base and a catalyst.

13. A process according to claim 12, wherein the solvent is dimethylformamide, the base is potassium 1,1-dimethylethylate and the catalyst is lithium bromide.

* * * * *